United States Patent
Glover

(10) Patent No.: US 6,711,547 B1
(45) Date of Patent: Mar. 23, 2004

(54) HANDHELD MEDICAL PROCESSING DEVICE STORING PATIENT RECORDS, PRESCRIPTIONS AND X-RAYS USED BY PHYSICIANS

(76) Inventor: Jason Corey Glover, 4403 Northside Pkwy., suite 1209, Atlanta, GA (US) 30327

( * ) Notice: Subject to any disclaimer, the term of this patent is extended or adjusted under 35 U.S.C. 154(b) by 0 days.

(21) Appl. No.: 09/514,541

(22) Filed: Feb. 28, 2000

(51) Int. Cl.$^7$ .............................................. G06F 17/60
(52) U.S. Cl. ................................ 705/2; 705/3; 600/300
(58) Field of Search .................... 705/2, 3; 600/300; 235/449, 454, 472; 379/88.22–88.27

(56) References Cited

U.S. PATENT DOCUMENTS

| | | | |
|---|---|---|---|
| 5,468,947 A | * 11/1995 | Danielson et al. | 235/472.02 |
| 5,867,821 A | * 2/1999 | Ballantyne et al. | 705/2 |
| 5,924,074 A | * 7/1999 | Evans | 705/3 |
| 6,161,095 A | * 12/2000 | Brown | 705/2 |
| 6,222,909 B1 | * 4/2001 | Qua et al. | 379/88.22 |
| 6,317,313 B1 | * 11/2001 | Mosgrove et al. | 361/680 |
| 6,388,870 B1 | * 5/2002 | Canova et al. | 361/683 |
| 6,396,481 B1 | * 5/2002 | Challa et al. | 345/169 |
| 6,421,650 B1 | * 7/2002 | Goetz et al. | 705/2 |
| 6,441,927 B1 | * 8/2002 | Dow et al. | 705/3 |

FOREIGN PATENT DOCUMENTS

WO  WO 01/88679 A2 * 11/2001 ............. G06F/1/16

OTHER PUBLICATIONS

Saran, Cliff, Hospital goes thin–client.)(Plymouth Hospital NHS Trust)(Company Operations), Computer Weekly, Dec. 2, 1999, p. 2.*

Anonymous, No. 5482827, File 16 (Gale Group PROMT®), "Epson Anoounces New Handheld Computer for Healthcare Industry; Epson's Innovative Footprint Supports More Accessories and Peripherals Than Any Other Handheld in its Class", Business Wire, Feb. 23, 1998,2 p.*

Jerney, John, No. 7804383, File 20 (Daily Global Reporter), "Nearing Reality: Wearable Computers", Yomiuri Shimbun/Daily Yomiuri, Oct. 19, 1999, 2 pages.*

* cited by examiner

Primary Examiner—Alexander Kalinowski
(74) Attorney, Agent, or Firm—Michael I Kroll

(57) ABSTRACT

A handheld medical processing device for providing a physician with medical information and storage for medical information. The medical processing device includes a processor and a memory unit within the device. A touch display screen is provided on a face of the device and connected to the processor. A recording device is provided for recording audio signals and a disk drive stores data input to the device on a recording medium by contacting the touch screen. The processor generates a menu of options for display on the display screen. Options for operation of the device are selectable by contacting the display screen at a display position of the desired menu option. The menu options allow the physician to input data by contacting the display screen, input audio data to be recorded by the recording device and prepare a prescription by contacting the display screen. The application software used by the processor is stored in the memory and data input on the touch screen is selectively saved in one of the memory or the recording medium. The memory also stores a database of medical information and the menu generated by the processor includes an option for accessing the database. An input/output port is also provided for connection of a peripheral device, the peripheral device is able to provide a scanned image to the processor for display, the device being able to increase and decrease the magnitude of the image.

4 Claims, 5 Drawing Sheets

HANDHELD MEDICAL PROCESSING DEVICE STORING PATIENT RECORDS, PRESCRIPTIONS AND X-RAYS USED BY PHYSICIANS

BACKGROUND OF THE INVENTION

1. Field of the Invention

The present invention relates generally to processors and, more specifically, to a hand held device able to provide a doctor with general medical information and specific patient information while also allowing input of notes regarding patients in both data and audio formats.

2. Description of the Prior Art

Numerous types of hand held processing devices have been provided in the prior art. For example, U.S. Pat. Nos. 5,468,947; 5,739,665 and 5,778,882 all are illustrative of such prior art. While these units may be suitable for the particular purpose to which they address, they would not be as suitable for the purposes of the present invention as heretofore described.

U.S. Pat. No. 5,468,947

Inventor: Arvin D. Danielson et al.

Issued: Nov. 21, 1995

A hand-held processing system wherein a peripheral module may receive therein a computer processor basic module of standardized construction, with a user-immune real-time multi-tasking operating system. Advantageously the peripheral module may include a touch screen or other highly versatile and compact data input/output device adaptable to graphical and/or other input/output modes suitable for different applications, languages and the like.

U.S. Pat. No. 5,739,665

Inventor: Steven John Bares

Issued: Apr. 14, 1998

A portable RF docking station is detachably coupled to a palm-sized computer to provide extended wireless communication through a radio modem and wireline communication through a wireline modem. Both modems are contained inside the docking station and are powered by rechargeable batteries. The docking station includes a housing having a flat platform, a side section that extends vertically upward along a side edge of the platform and a rear section that extends vertically upward along a rear edge of the platform. The housing in combination with a data connector holds the computer and docking station together as one cohesive unit. A four-stage charging circuit maintains the rechargeable battery in a fully charged condition.

U.S. Pat. No. 5,778,882

Inventor: Stephen A. Raymond et al.

Issued: Jul. 14, 1998

A health monitoring system which tracks the state of health of a patient and compiles a chronological health history of the patient uses a multiparamedic monitor which periodically and automatically measures and records a plurality of physiological data from sensors in contact with the patient's body. The data collected is not specifically related to a particular medical condition but, instead, provides the information necessary to derive patterns which are characteristic of healthy patients as well as those who are ill. The data collected is periodically uploaded to a database in which it is stored along with similar health histories for other patients. The monitor is preferably self-contained in a chest strap which is located on the patient's torso, and makes use of a controller which controls sampling of the desired data and storage of the data to a local memory device pending uploading to the database. The more voluminous data collected is reduced and compressed prior to storage in the local memory device. Preferably, much of the monitor circuitry is run intermittently to conserve power. The monitor data is supplemented with subjective data (such as psychological and environmental conditions) collected from the patient using a handheld data input device which runs a program to solicit information from the patient. The subjective data collected is chronologically aligned with the monitor data in the database such that the health history of a patient includes both objective and subjective medical data.

SUMMARY OF THE PRESENT INVENTION

The present invention relates generally to processors and, more specifically, to a device able to provide a doctor with general medical information and specific patient information while also allowing input of notes regarding patients in both data and audio formats.

A primary object of the present invention is to provide a medical processing device that will overcome the shortcomings of prior art devices.

Another object of the present invention is to provide a medical processing device which is able to aid doctors in examining a patient.

A further object of the present invention is to provide a medical processing device which is able to display medical information to a doctor while examining a patient.

A yet further object of the present invention is to provide a medical processing device including a touch screen and a contact pen whereby the doctor is able to input data regarding a patient by contacting the touch screen with the contact pen.

A still further object of the present invention is to provide a medical processing device including a recording device for recording audible notes regarding a patient.

A further object of the present invention is to provide a medical processing device having an input port for connection to a scanning device for scanning medical information, charts and x-rays into memory for viewing by a doctor.

A still further object of the present invention is to provide a medical processing device able to zoom in and zoom out on an image or x-ray being displayed on the touch screen.

A yet further object of the present invention is to provide a medical processing device able to automatically clean up an image or x-ray being displayed on the touch screen.

Another object of the present invention is to provide a medical processing device able to display a prescription pad on the display screen for use by a physician in writing out a prescription using the contact pen, the prescription being able to be printed by connecting the device to a printer through the input/output port.

Another object of the present invention is to provide a medical processing device that is simple and easy to use.

A still further object of the present invention is to provide a medical processing device that is economical in cost to manufacture.

Additional objects of the present invention will appear as the description proceeds.

A handheld medical processing device for providing a physician with medical information and storage for medical information. The medical processing device includes a processor and a memory unit within the device. A touch display screen is provided on a face of the device and connected to the processor. A recording device is provided for recording audio signals and a disk drive stores data input to the device on a recording medium by contacting the touch screen. The processor generates a menu of options for display on the display screen. Options for operation of the device are selectable by contacting the display screen at a display position of the desired menu option. The menu options allow the physician to input data by contacting the display screen, input audio data to be recorded by the recording device and prepare a prescription by contacting the display screen. The application software used by the processor is stored in the memory and data input on the touch screen is selectively saved in one of the memory or the recording medium. The memory also stores a database of medical information and the menu generated by the processor includes an option for accessing the database. An input/output port is also provided for connection of a peripheral device, the peripheral device is able to provide a scanned image to the processor for display, the device being able to increase and decrease the magnitude of the image.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

DETAILED DESCRIPTION OF THE PREFERRED EMBODIMENT

Figure 1:
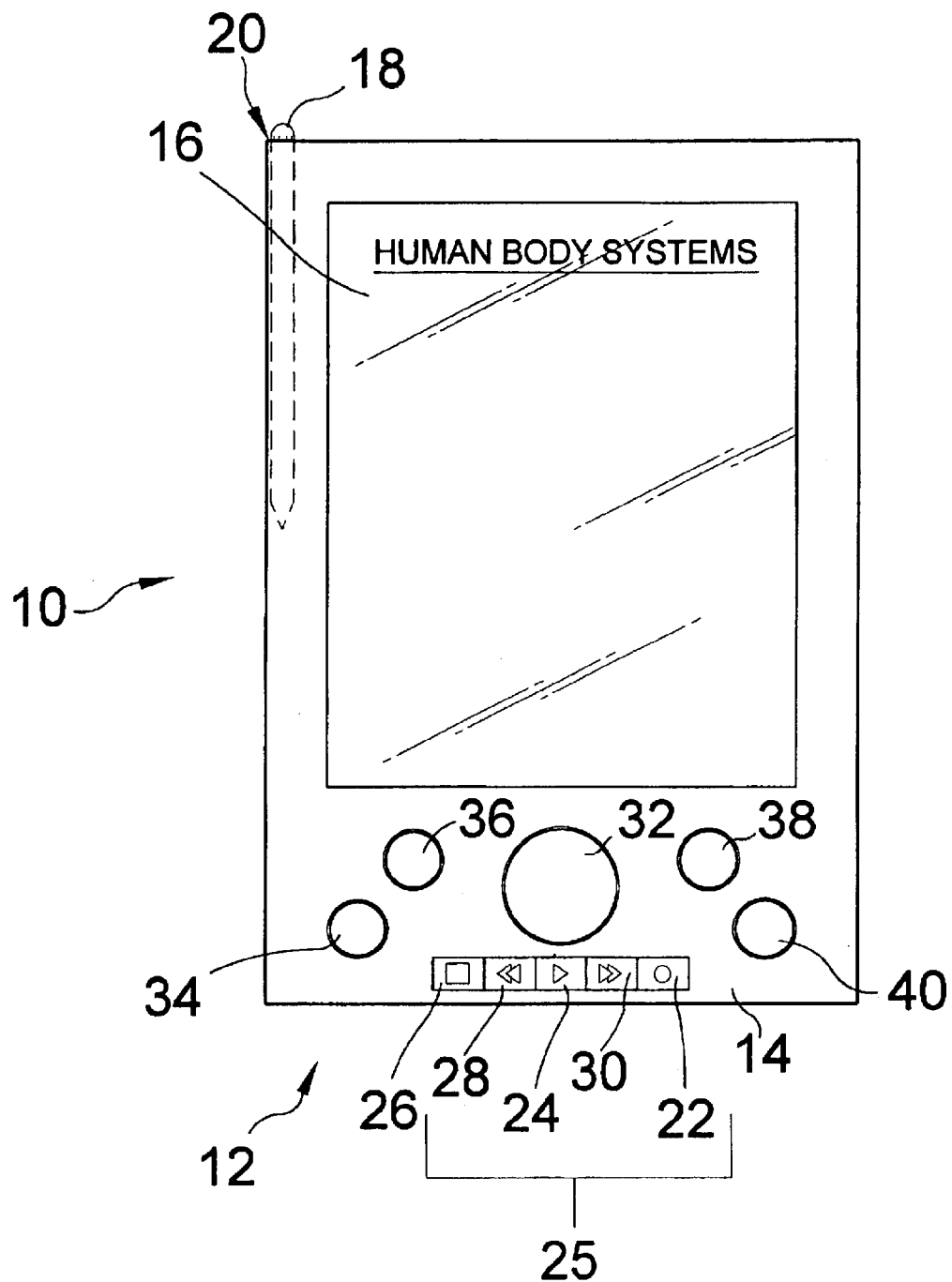
FIG. 1 is a front perspective view of the medical processing device of the present invention.

Turning now descriptively to the drawings, in which similar reference characters denote similar elements throughout the several views, FIGS. 1 through 5 illustrate the medical processing device of the present invention indicated generally by the numeral 10.

Figure 3:
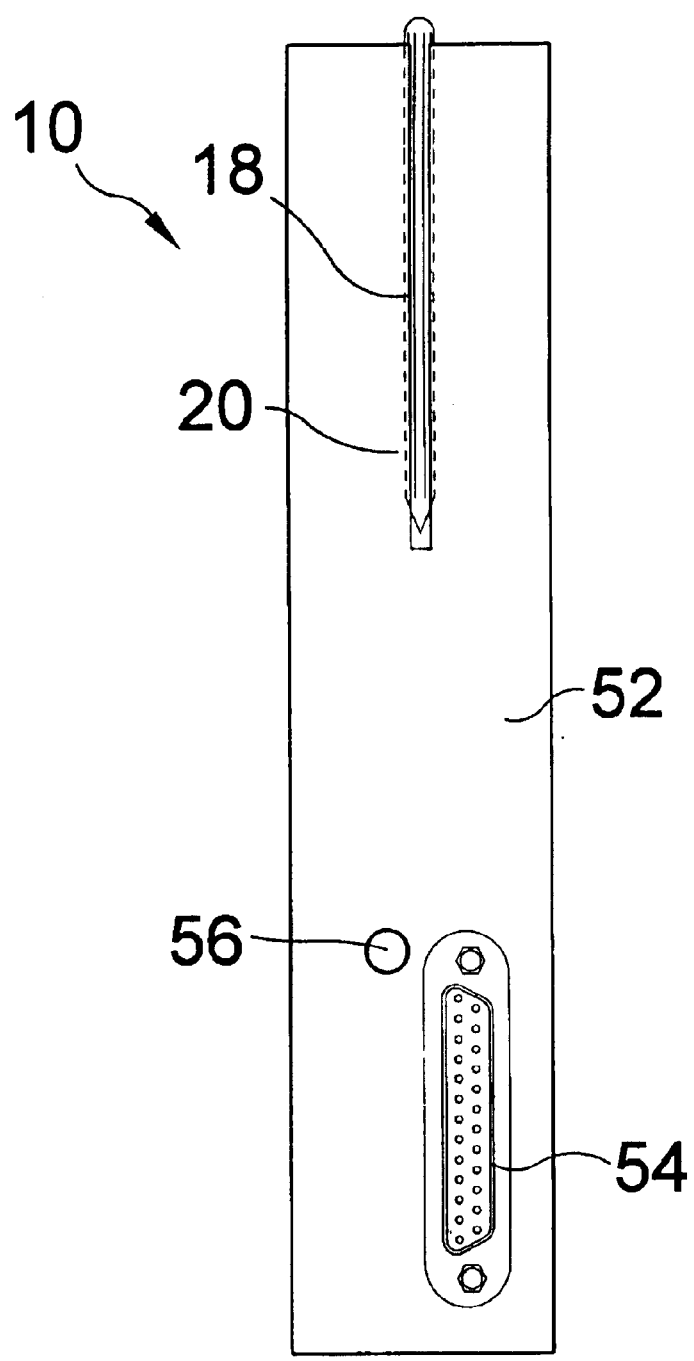
FIG. 3 is a left side view of the medical processing device of the present invention.

The medical processing device 10 is shown in FIG. 1 and includes a housing 12 having a face side 14. A display screen 16 is positioned on the face side 14. The display screen 16 is a touch screen on which data can be entered through contact by an object. Contact is preferably made using a contact pen 18 provided with the medical processing device 10. A recess 20 shown in FIG. 3 is positioned extending into the housing 12 from a top side thereof. The contact pen 18 is selectively received by the recess 20.

Positioned on the face side 14 of the housing 12 are a plurality of control buttons. A group of recording control buttons 25 are provided for controlling an audio recording device. A record button 22 is provided for initiating recording of an audio message and a play button 24 for initiating playback of a recorded message. A stop button 26 is provided for ceasing operation of the audio recording device. A rewind button 28 is provided for rewinding or moving to a previously recorded portion of a recording medium within the recording device and a fast forward button 30 is provided for forwarding through the recording medium. The audio signals recorded by the medical processing device 10 may be recorded on a diskette received by the device or in a memory unit within the medical processing device 10.

A menu button 32 is provided on the face side 14 of the housing 12 for displaying a menu of options on the display screen 16 for performing different functions with the medical processing device 10. A zoom button 34 is provided for zooming in or zooming out an image displayed on the display screen 16. A save button 36 is provided for readily saving any information input to the medical processing device 10. A cursor is provided on the display screen 16 and is around the display screen 16 using a cursor movement button 38. This button 38 may be either in the form of an eraser head or ball for moving the cursor all around the screen or a press button which will move the cursor down one screen line each time the button 38 is pressed. A menu select button 40 is provided for selecting a desired and highlighted menu option on the display screen 16.

Figure 2:
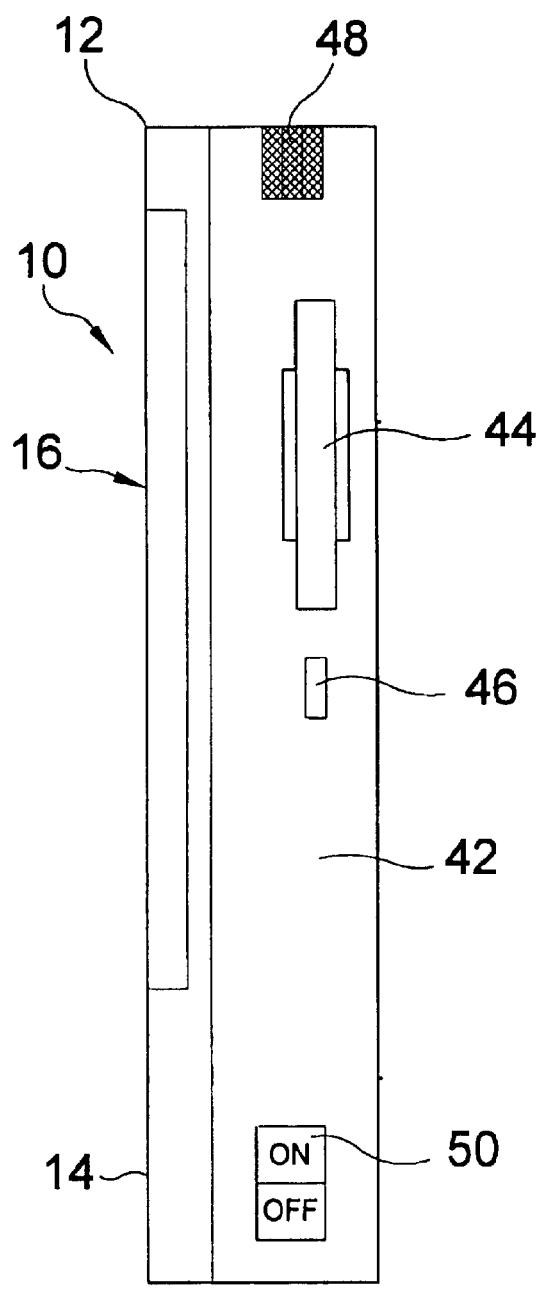
FIG. 2 is right side view of the medical processing device of the present invention.

A view of a right side 42 of the medical processing device 10 is illustrated in FIG. 2. Positioned on the right side 42 is a disc drive 44 for insertion of a diskette on which data can be stored and read. An eject button 46 is positioned adjacent the disk drive 44 for ejecting a diskette from within the disk drive 44. A microphone 48 is provided for receiving an audible signal to be stored on a recording medium when the record button 22 of the recording device is activated. A power button 50 is provided for turning the medical processing device 10 on and off.

A view of the left side 52 of the medical processing device 10 is illustrated in FIG. 3. Positioned to extend along a portion of and parallel to the left side 52 is a recess 20 for receiving a pen 18. An input/output port 54 is provided on the left side 52 for connection of a peripheral device such as a printer or a scanner. A control button 56 is provided for activation of a prescription pad algorithm. This algorithm will display a prescription pad on the display screen 16 and the physician can then use the pen 18 to write out a prescription on the touch display screen 16. Alternatively, an option to initiate operation of the prescription pad algorithm may be provided in the menu list and activated through selection of the option using the cursor movement button 38 and option select button 40.

Figure 4:
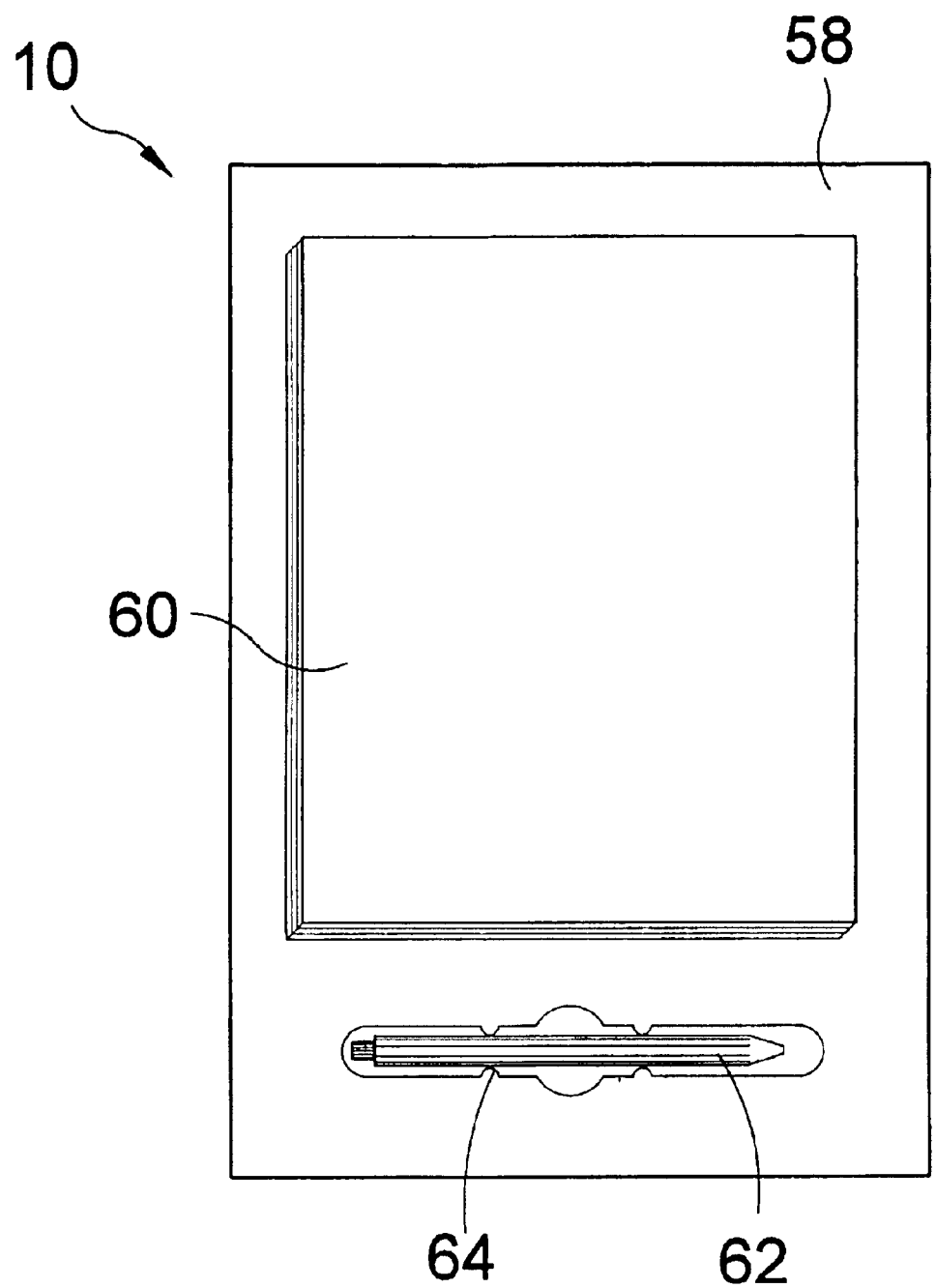
FIG. 4 is a back side perspective view of the medical processing device of the present invention.

A back side 58 of the medical processing device 10 is illustrated in FIG. 4. Positioned on the back side is a retaining clip 62. The retaining clip 62 is provided for releasably retaining a pen 64 therein. The pen 64 allows the physician using the medical processing device 10 to write information down on a pad or chart of a patient as the examination is taking place. An optional pad 60 may be provided releasably connected to the back side 58 for use by a physician to jot down notes.

Figure 5:
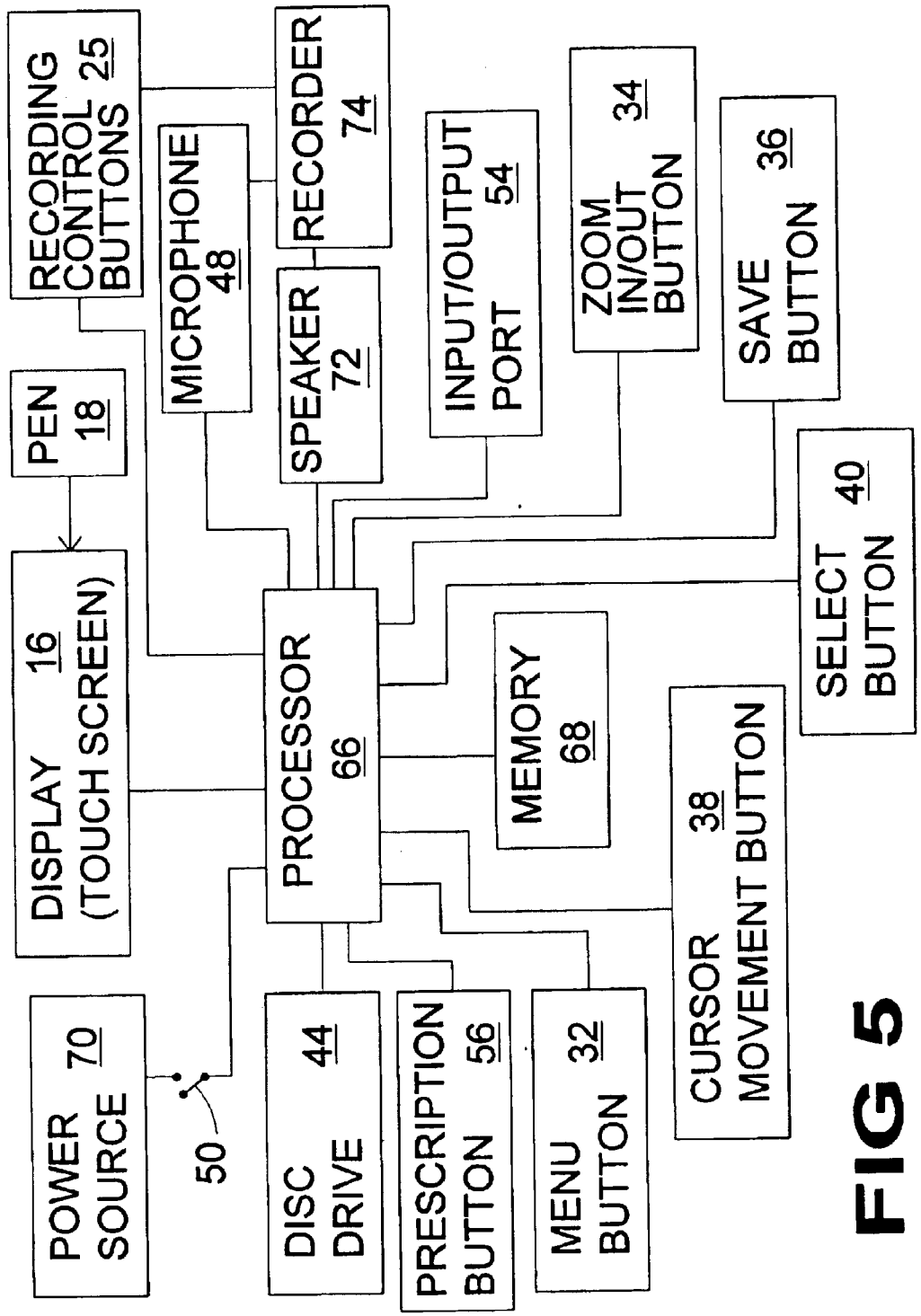
FIG. 5 is a block diagram of the medical processing device of the present invention.

A block diagram of the elements forming the medical processing device 10 is illustrated in FIG. 5. As can be seen from this figure, the medical processing device 10 includes a processor 66 and a memory unit 68 connected thereto. The memory unit 68 stores all the programs to be executed by the processor 66 and all data input to the medical processing device 10 by a physician using the medical processing device 10. An internal power source 70 is connected to the processor 66 via the power on/off button 50. The display screen 16 and disc drive 44 are also connected to the processor 66. The display screen 16 is used to both input data to the processor 66 and to display data provided by the processor 66. The contact pen 18 is provided to input data to the processor 66 through the display screen 16 by making contact with the display screen 16. The disk drive 44 is able to both be read by the processor 66 providing information to the processor 66 and store data provided by the processor 66. A recording device 48 is positioned within the housing 12 of the medical processing device 10 for recording audio signals such as the voice of the physician using the medical processing device 10 when taking oral notes. The recording device 74 is shown as being directly connected to the processor 66 for recording audio signals received by the processor 66 through the microphone 48. Alternatively, the microphone 48 may be directly connected to the recording device 74. The audio signals may also be recorded on a diskette received by the disk drive 44. A speaker 72 is connected to both the processor 66 and recording device 74 for providing audible signals representative of the audio signals recorded on a recording medium. The recording control buttons 25 are connected to at least one of the processor 66 and the recording device 74 for controlling the recording and playback of audio data. The input/output port 54 is provided for connection of a peripheral device to the medical processing device 10. The input/output port 54 may be used to connect a printer to the medical processing device 10 for printing out data stored on by the processor 66 in the memory or printing the image displayed on the display screen 16 such as a prescription. A scanner may also be connected to the input/output port for scanning in data such as x-rays of patients for viewing by the physician. The zoom in/out button 34 is provided for magnifying or demagnifying an image on the display screen 16 such as an x-ray scanned into the medical processing device 10.

The menu button 32 is connected to the processor 66 for activating the menu program stored in the medical processing device 10. The menu program displays a menu of features provided by the medical processing device 10 on the display screen 16 which may be selected for activation by the user/physician. The cursor movement button 38 moves a cursor around the display screen 16 highlighting respective options within the menu displayed upon activation of the menu program. The select button 40 is connected to the processor 66 for selecting a menu option highlighted by the cursor. A save button is provided for saving data input to the medical processing device 10 either through a peripheral device, the disk drive 44 or contact of the display screen 16.

The operation of the medical processing device 10 will now be described with reference to the figures. In operation, the medical processing device 10 is used by a physician to view and store medical information regarding patients, input medical data regarding patients, record audio notes for patients, produce prescriptions and receive general medical information. The device includes a disk drive 44 for receiving a diskette and storing data regarding a patient on the diskette. Alternatively, the data may be stored within the medical processing device 10. An input/output port 54 is provided for connection of peripheral devices such as printers, scanners and external memory devices for inputting data to and outputting data from the medical processing device 10. To begin using the device, the physician will activate the power switch 50 to connect the processor 66 to the power source 70. The power source 70 is preferably an internal, rechargeable power source thereby allowing the physician to move about with the medical processing device 10. When not in use the power source 70 may be connected to an external battery to be recharged for future use. Alternatively, the power source can be an external power source connected to the medical processing device 10 via a connection wire. Once the power button 50 is activated, the medical processing device 10 will "boot up" loading the programs stored therein for use. A start up menu of options will be displayed on the display screen 16. This menu includes features including but not limited to access patient information, record audio signals, access medical database, view scanned images, fill out prescription, print data, etc. . . .

The physician will select an option on the menu by activation of the cursor movement button 38 on the face side 14 of the medical processing device 10. A cursor is provided on the display screen to highlight a selective menu option. Use of the cursor movement button 38 will move the cursor around the display screen 16 highlighting different options within the menu. Upon highlighting the desired menu option, the physician will then activated the cursor select button 40. Activation of this button will open the desired application program or perform the desired action. Alternatively, certain functions have an individual control button on the face side 14 of the housing 12.

The physician may enter a word processing application in which notes may be taken regarding a particular patient. The display screen 16 is a touch screen, thus contact with the display screen will generate an image thereon which may be saved. The contact pen 18 is provided with the medical processing device 10 for contacting the display screen 16 and is selectively received by the recess 20 extending into the housing 12. The contact pen 18 is removed from within the recess 20. The physician will use the contact pen 18 in a manner similar to a conventional writing instrument while writing on the display screen 16. As the pen 18 moves along the display screen 16, an image will be generated on the display screen 16 following the movements of the pen 18. The notes produced on the display screen 16 can be saved onto a diskette by pressing the save button 36 on the face side 14 of the housing 12.

The physician is also able to create a prescription by either selecting the prescription option on the menu or by activating the prescription button on the housing 12. Activation of this function will display a simulated prescription pad on the display screen 16. The physician will then use the contact pen 18 to write out a prescription. Once completed, the physician will connect the medical processing device 10 to a printer through the input/output port 54 and print out the prescription. The image from the display screen 16 will be printed by the printer and thus the prescription will appear as if the physician had written it himself.

Audio notes can be recorded by selecting the audio note option from the menu list or by activating any of the audio recording control buttons 25. This will operate as a conventional audio recording device and record audio data received through the microphone 48 on either a diskette within the disk drive 44, a separate recording medium inserted into the medical processing device 10, a recording medium within a separate device connected to the medical processing device 10 via the input/output port 54 or onto the internal memory unit 68 within the medical processing device 10. The recorded data may be replayed by the medical processing device 16 through the speakers 72.

A scanner may be connected to the medical processing device 10 through the input/output port 54. By selection of the scanner option on the menu, images may be canned into the medical processing device 10, viewed on the display screen 16 and saved in memory, a diskette or other recording medium. The processor 66 will be able to enhance the scanned in image automatically using software stored in the memory unit 68. The software is activated upon selection of the scanner option from the menu. The physician may zoom in on a specific area of the scanned image for better examination of a portion of the image or zoom out on the image to obtain a full scale or larger view of the image using the zoom in/out button 36. An example of an image to be scanned into the medical processing device 10 would be x-rays of patients for either viewing or adding to a medical history file for the patient. The images may be saved to a desired location by activating the save button 34.

The menu may be displayed at any time by activating the menu button 32. The physician may also take written notes with the pen 62 releasably connected to the back side 58 of the medical processing device 10 by the clip 64. The pad 60 is releasably connected to the back side 58 for jotting down notes.

Stored within the memory unit 68 is a database of medical information. The physician is able to access this database to obtain medical information which may be needed to diagnose a medical condition by selecting the relevant menu option from the menu using the cursor movement button 38 and cursor select button 40. This will provide physicians with a database of medical information at their fingertips. The database will be provided in accordance with a software program which will prompt the user to select the desired topic using either the cursor movement button 38 or the contact pen 18 to select functions such as help and to sift through different topics and subtopics.

Each of the different menu options are controlled by software. The software provides numerous options to make the medical processing device 10 user friendly including an extensive database full of helpful topics which may be selected from the main menu. The main menu, as previously stated, is displayed on the display screen 16 upon turning the medical processing device 10 on or by pressing the menu button 32. The main menu can be accessed from any application by pressing the menu button 32.

When the physician is finished with the examination, any data desired to be recorded is saved. If the physician prepared a prescription, then the medical processing device 10 is connected to a printer through the input/output port 54 and the prescription is printed and given to the patient to fill. The physician will then turn the medical processing device 10 off by pressing the power button 50. The medical processing device 10 is then stored until use is desired again. If the medical processing device 10 is provided with an internal power source 70 the power source is recharged upon completing use by connecting the power source 70 to an external source.

From the above description it can be seen that the medical processing device of the present invention is able to overcome the shortcomings of prior art devices by providing a medical processing device which is able to aid physicians in examining a patient and display medical information to the physician while examining a patient. The medical processing device includes a touch screen and contact pen whereby the physician is able to input data regarding a patient by contacting the touch screen with the contact pen and a recording device for recording audible notes regarding a patient. The medical processing device also includes an input port for connection to a scanning device for scanning medical information, charts and x-rays into memory for viewing by a doctor. The medical processing device is able to automatically clean up an image or x-ray being displayed on the touch screen and to zoom in and zoom out on the image or x-ray displayed on the touch screen. The medical processing device is also able to display a prescription pad on the display screen for use by a physician in writing out a prescription using the contact pen, the prescription being able to be printed by connecting the device to a printer through the input/output port. Furthermore, the medical processing device of the present invention is simple and easy to use and economical in cost to manufacture.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A handheld medical processing device for providing a physician with medical information and storage for medical information, said medical processing device consisting of:
   a) a housing;
   b) a processor within said housing;
   c) a memory unit within said housing and connected to said processor;
   d) a touch screen display connected to said processor and provided on a face side of said housing;
   e) means within said housing for recording audio signals provided by a physician; and
   f) means for storing data input by the physician by contacting said touch screen, wherein said processor generates a menu of options for display on said display and selectable by contacting said display screen at a position at which the desired menu option is displayed to allow the physician to input data using the display screen, input audio data to be recorded by said recording means, prepare a prescription on said display screen by contacting said display screen with a pointed instrument, wherein application software used by said processor is stored in said memory and data input on said touch screen is selectively saved in one of said memory or a recording medium received by said data storing means;
   g) said memory storing a database of medical information and said menu generated by said processor includes an option for accessing said database upon contacting said display screen at a position at which said menu option is displayed;

h) an input/output port for connection of a peripheral device, the peripheral device providing data to said processor including a scanned x-ray image to the processor for display on said display screen and for adding to a medical history of a patient in said device;

i) a zoom in/out button connected to said processor for increasing or decreasing the magnitude of the x-ray image on the display screen, said processor being able to enhance the image received from the peripheral device;

j) a prescription button for controlling said processor to activate a prescription application and display an image of a prescription on said display screen;

k) a clip on a back side of said housing for selectively receiving a writing instrument and a pad selectively connected to the back side of said housing;

l) an audio recording device for recording audio signals input by the physician and a plurality of recording control buttons positioned on said housing for controlling operation of said audio recording device said recording control buttons include any combination of a record button, a play button, a stop button, a rewind button and a fast forward button; and m) a microphone connected to said audio recording device and positioned on said housing for receiving audio signals from the physician and a speaker for generating audio signals representative of audio data recorded by said audio recording device when said play button is activated.

2. The medical processing device as recited in claim 1, wherein the peripheral device is able to provide a hard copy of data provided thereto by said processor through said input/output port.

3. The medical processing device as recited in claim 1, further comprising a recess extending through at least a portion of the housing and a contact device selectively received by said recess for use in contacting said display screen.

4. The medical processing device as recited in claim 3, wherein said contact device is a pen shaped device.

* * * * *